United States Patent
Bley

(12) 
(10) Patent No.: US 6,600,970 B2
(45) Date of Patent: Jul. 29, 2003

(54) METHOD OF ESTABLISHING SYNTHESIS PATHS

(75) Inventor: Klemens Bley, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/945,732

(22) Filed: Sep. 5, 2001

(65) Prior Publication Data

US 2002/0049516 A1 Apr. 25, 2002

(30) Foreign Application Priority Data

Sep. 6, 2000 (DE) .......................................... 100 43 853

(51) Int. Cl.⁷ ............................................... G05B 21/00
(52) U.S. Cl. ............................ 700/268; 702/27; 707/3; 260/1; 422/187
(58) Field of Search ........................... 700/268; 702/27; 707/3; 260/1; 422/187

(56) References Cited

U.S. PATENT DOCUMENTS

| | | | | | |
|---|---|---|---|---|---|
| 4,473,890 | A | * | 9/1984 | Araki | 702/27 |
| 4,642,762 | A | * | 2/1987 | Fisanick | 707/104.1 |
| 4,747,059 | A | * | 5/1988 | Hirayama et al. | 703/12 |
| 4,811,217 | A | * | 3/1989 | Tokizane et al. | 707/3 |
| 4,939,666 | A | * | 7/1990 | Hardman | 436/86 |
| 5,418,944 | A | * | 5/1995 | DiPace et al. | 702/27 |
| 5,463,564 | A | * | 10/1995 | Agrafiotis et al. | 260/1 |
| 5,511,186 | A | * | 4/1996 | Carhart et al. | 707/2 |
| 5,577,239 | A | * | 11/1996 | Moore et al. | 702/27 |
| 6,159,255 | A | * | 12/2000 | Perkins | 250/339.7 |

OTHER PUBLICATIONS

Ihlenfeldt et al., "Hash codes for the identification and classification of molecular structure elements", J. Computational Chemistry, 15(8), 793–813 (1994).*
Prickett et al., "Construction of complex reaction systems—II. Molecule manipulation and reaction application algorithms", Computers chem. Engng. 21(11), 1237–1254 (1997).*
Cringean et al., "Subgraphs of reduced chemical graphs as screens for substructure searching of specific chemical structures",J. Information Science 15 (1989) 211–222.*
DeLaet et al., "Finding drug candidates in virtual and lost/emerging chemistry", J. Heterocycl. Chem. 37(3), 669–674 (May–Jun. 2000).*
Iizuka et al., "Graph theoretical studies of molecular structures IX. Searches for the neighbourhood of pentagonal dodecahedrane", Gunma Daigaku Kyoikugakubu Kiyo, Shizen Kagaku Hen (1981), 30, 5–12.*
http://www.beilstein.com/products/xfire/.*
http://www.accelrys.com/chem_db/mos.html.*
http://www.risc,uni–linz.ac.at/pepole/blurock/document/documet.html.*

* cited by examiner

Primary Examiner—Mark L. Bell
Assistant Examiner—Jennine M. Brown
(74) Attorney, Agent, or Firm—Millen, White, Zelano & Branigan, P.C.

(57) ABSTRACT

A method of establishing a synthesis path in a multiplicity of potentially interlinakable reactions, and a computer program to prepare a synthesis path.

10 Claims, No Drawings

METHOD OF ESTABLISHING SYNTHESIS PATHS

The present invention concerns a method of establishing synthesis paths in a multiplicity of potentially interlinkable reactions. In the chemical industry, for carrying out a method or for improving methods, the man skilled in the art is frequently confronted with the problem of having to produce given products or intermediate products without those products being commercially available readily and rapidly or of the desired quality.

In the case of a large number of the chemical substances which are known in the meantime however the man skilled in the art is in no way familiar with the conceivable ways of synthesising any given product. Admittedly, in some circumstances there are reference works in which it is possible to find information about the manufacture of a given product, but in that respect it is completely unknown whether the way in question is also a meaningful one in a practical context, in particular whether it is economically meaningful, and what disadvantages it possibly entails. In addition it is often not possible for the man skilled in the art to foresee which possible consequential reactions can take place when he has manufactured a given product, even if this may involve a by-product or waste product.

The present invention seeks to afford a remedy there insofar as if required it affords the man skilled in the art a complete overview over all conceivable or known synthesis paths which can result in a given product or which can start from an educt. In this respect that product may also be only an intermediate product for further chemical reactions, which intermediate product however is not readily available.

In consideration of that state of the art the object of the present invention is to provide a method of establishing synthesis paths, which substantially automatically furnishes a chain or also a branched network or a tree of various reactions, from which all synthesis paths known in the stored system can be directly read off or represented, which result in a given product or which start from a predetermined educt.

In accordance with the invention therefore both all conceivable educts and products and also all reactions from said educts and products are carefully acquired and encoded, that is to say stored with a unique designation or identification. On the basis of encoded storage both of the potential products and educts and also the corresponding reactions, in a first review of the database all reactions are acquired, in which for example the selected product appears on the product side. Those reactions also include references to or codes in respect of the corresponding educt or educts which are sought in a next following review step as products of other reaction equations. For that purpose also once again the reactions and the educts involved therein are ascertained, so that a stepwise procedure involves progressively acquiring educts whose reaction results in intermediate products which once again in a reaction with other products or other intermediate products ultimately result in the product being sought. As in general terms reactions between certainly different combinations of educts can result in one and the same product, there is in general a branched network or a tree structure of reactions, wherein the root is formed by the product being sought (or educt) and the branches and twigs of the tree structure correspond to products or intermediate products while all branching points and connections correspond to reactions.

In that way the result obtained is at least one but generally a plurality of reaction chains which in addition are heavily networked with each other, which means that it is possible to change from one reaction chain to another in order to arrive at the selected product. Under some circumstances that can be desirable if there is a wish to avoid undesired intermediate products along a given first reaction chain or if that appears to be expedient for other reasons, as will be still more clearly apparent from the preferred embodiments and the illustration of an example.

Desirably the reactions are stored in encoded fashion in such a way that their code also includes the codes of the products and educts involved in the reaction. In that way it is possible to read off directly at the reactions or the encodings of the reactions, which educts and products are involved therein. That makes it easier in particular to acquire all reactions in which for example a given product (or educt) is involved. The reactions then only need to be investigated to ascertain whether for example on their product side they include the encoding of the product in question. If yes, then the reaction is part of a desired reaction chain, if no, it can be rejected for the intended situation.

It is also desirable if allocated to the reactions and/or the educts or products are a respective one or also a plurality of evaluation parameters which, by setting a selection criterion for the parameter value, make it possible to implement a selection to the effect of whether the parameter for a reaction or a product falls below or rises above a predetermined parameter value (possibly also a predetermined sum or a product of parameter values). When representing reaction chains, corresponding reactions and products which fall below or exceed a corresponding evaluation scale can each be so identified that it is possible to perceive that they have fallen below or risen above the evaluation scale, for example by coloured underlining.

The preferred embodiment of the invention provides that the parameters are also stored of part of the codes. For example a code could be a number having a plurality of digits, which characterises on the one hand a chemical substance, wherein moreover a plurality of digits of the number are reserved for parameters which could assume numerical values between for example 1 and 10 or 0 and 1.

Parameters which are used for evaluation of products or reactions can include for example measurement numbers for the following properties: toxicity, reaction conditions, apparatus expenditure, yield, costs of manufacture and/or procurement, stability of the educts/products, and handleability of the educts/products.

By way of example it could be the case that a possible reaction chain contains a reaction which can take place only under very high pressure and at very high temperature, which denotes a correspondingly high level of apparatus expenditure. In addition for example educts can be involved in reactions, which cannot be manufactured readily or not at viable expense with their own means (in accordance with a corresponding reaction chain) so that the procurement costs are also involved as parameters in the evaluation. A preferred operating procedure when using the method according to the invention will be clearly apparent from the following representation of an embodiment by way of example.

The invention includes a method of establishing synthesis paths comprising the following steps:
  a) constructing a first database with the educts and products which are wanted for the purpose of use,
  b) allocating a unique code to each of the educts and products and storing the codes with allocations in the first or a further database,
  c) constructing a second database with the largest possible number of reactions in which the stored educts and/or products occur, d) selecting one or more educts or products,
e) searching through the second database for all reactions in which the one or more selected educts and/or products occur, in a first review step, and effecting intermediate storage of said reactions,
f) searching through the second database for all reactions in which the educts and/or products of the reactions occur, which were found and put into intermediate storage in the first review step, and effecting intermediate storage of the reactions obtained in that case,
g) possibly continuing the review procedure in further steps in order to obtain the reactions in which the additional educts and/or products ascertained in the preceding stage appear, and
h) reproducing at least one reaction chain and/or reaction tree which extend over the obtained reactions of the various review stages and which contain the one or more selected educts or products.

The reactions can be stored encoded in such a way that their code contains the encodings of the educts and products involved in the reaction.

One or more evaluation parameters, can be allocated to the reactions and/or educts and products, which by setting of a selection criterion for the parameter permit a selection of reactions in a chain or a branched reaction tree.

The parameters or parameter values can be stored as part of the code.

The parameters can be selected as measurement numbers for one or more of the following properties: toxicity, reaction conditions, apparatus expenditure, yield, costs of manufacture and/or procurement, stability of the educts/products, and handleability of the educts/products.

Using an optimization program with weighting of the parameter values one or more optimized synthesis parts can be ascertained and represented.

Even without further explanation it is assumed that a man skilled in the art can use the above description in its broadest extent. The preferred embodiments and examples are accordingly to be interpreted only as a descriptive disclosure and in no way as a disclosure limiting the invention in any way.

The embodiment set forth hereinafter is restricted to a very small set of symbolically reproduced substances and reactions. By way of example there are set forth twelve different substances (or molecules) A to N which are encoded and stored in accordance with the following table with figures from 01 to 12.

| A | ↔ | 01 |
| B | ↔ | 02 |
| C | ↔ | 03 |
| D | ↔ | 04 |
| E | ↔ | 05 |
| F | ↔ | 06 |
| G | ↔ | 07 |
| H | ↔ | 08 |
| K | ↔ | 09 |
| L | ↔ | 10 |
| M | ↔ | 11 |
| N | ↔ | 12 |

The foregoing codes are stored in a database.

In addition the following reactions are known and stored, in which said substances A to N are involved:

| I | A + B → | C + D |
| II | D + E → | F + G |
| III | G + B → | H + K |
| IV | A + F → | L + M |
| V | C + L → | N + K |

The foregoing reactions could be written for example as follows in a numerical code:

| I | 01-02-03-04 |
| II | 04-05-06-07 |
| III | 07-02-08-09 |
| IV | 01-06-10-11 |
| V | 03-10-12-09 |

The substance K is a substance which is being sought and whose synthesis paths are to be ascertained. The substance K is encoded with the figure 09.

The user would now input for example in a suitable search field either the usual chemical designation for which the letter K stands here, or the corresponding numerical code, in this case 09. In accordance with the method of the invention, a search for all reactions in which the code 09 emerges on the product side would now begin in a database of the stored reactions. It should be pointed out once again at this juncture that the above example is very greatly simplified insofar as it uses only two-digit codes, a very restricted number of chemical substances and a very restricted number of chemical reactions, in which in addition the procedure only ever involves the storage of reactions in which two products result from two educts, so that it is clear that the first two codes of a reaction equation always reproduce the educts and the third and fourth codes reproduce the products. It will be appreciated that it would also be possible to store more complicated reactions with more reaction partners and also specifying catalysts, in which respect the product side and the educt side would have to be respectively separate from each other by a suitable marking.

When searching through the reaction database the system encounters equations III and V which on the product side have the figure code 09, that is to say the substance K.

That results overall in the following possible reactions paths for the substance K, which are reproduced hereinafter by the sequence of the reaction equations I to V.

I–II–III

I–II–IV–V

I–V

If the educts F and L are not directly available as starting substances because for example they are not storable or are unstable, then the shortest reaction path I–V does not apply.

As will be readily seen, a further branching is obtained in the first two chains in relation to equation II by using either the product G of the reaction II together with B as educts of the reaction III in order to obtain the products H and K, or, by way of two further reactions IV and V from the reaction II, using the product F in accordance with reaction equation IV in order to use the resulting intermediate product L in accordance with reaction equation V and then obtaining the products N and K.

It is apparent for men skilled in the art that the number of possible synthesis paths is generally very much greater and that the synthesis paths in practice are still very much more greatly branched and networked than in the example illustrated herein. For example, besides the path I–V, there may certainly also be other independent paths in order to arrive at the educts C and L of the equation V, which however are not reproduced here.

Synthesis path I–II–III, after I–V, initially appears as the next shortest and in that respect the one which most suggests itself, at least if it is assumed that the starting educts A and B as well as E are easily obtainable and available. It could however be the case for example that the product H occurring in reaction III can be very troublesome insofar as for example it is toxic or can be separated from product K only with very great difficulty. It would also be conceivable that reaction III can be implemented only at considerable apparatus expenditure.

Ultimately that means that, on the foregoing assumptions, the synthesis path I–II–IV–V is the most effective and economically most meaningful synthesis path.

Insofar as the choice of the synthesis paths is not apparent and obvious to the man skilled in the art, it seems desirable also to include in the reaction codes and possibly also in the substance codes parameters which classify the reactions and substances from different points of view and which permit evaluation in the selection of the reaction paths. For example toxic substances could have a parameter which provides that some products or educts are underlined in colour or emphasised in some other way in the representation of those substances, that is to say either in the code representation or in some other usual identification. Reactions which for example take place only at high pressure and/or at high temperature could also be identified by corresponding coloured underlining. It will be appreciated that simple additional information in the form of a numerical code, an abbreviation or also clear text which indicate to the user which portions of reaction paths should be as far as possible avoided are also conceivable.

Finally, with the method according to the invention it is also possible with a suitable evaluation program to automatically generate and represent the synthesis path which is most economical or most meaningful from various points of view, for example on a display screen or in the form of a printout with a sequence of reaction equations and stating the required starting substances and method parameters.

For that purpose it is only necessary for the individual parameters to be suitably established and also weighted in relation to each other and in regard to the desired boundary conditions. It may for example be the case that, under specific operating conditions, the toxicity of a product is of subordinate significance as the reaction takes place in any case in a closed-off system and the toxic substance is then 100% re-used or however can be very easily neutralised in consequential reactions. In such a case only a very slight significance would be attributed to the toxicity of that substance. That can be stored or noted in a suitably encoded form in the associated reaction equation.

The method according to the invention makes it possible in a very simple and rapid fashion to obtain a complete overview over all synthesis paths which result in a given product, and in that way also permits rapid selection of the synthesis paths which are most desirable from the practical and economic points of view and which could possibly only be found with difficulty in some other fashion. It will be appreciated that the system can also be used in the same manner in order to establish in relation to a given group of educts or also in relation to an individual educt as the starting point, what possible end products are to be produced therefrom.

What is claimed is:

1. A method of establishing one or more synthesis paths by a computer comprising:
    a) constructing a first database of educts and products,
    b) allocating a unique code to each of the educts and products and storing the codes with allocations in the first or a further database,
    c) constructing a second database of reactions in which the stored educts and/or products occur,
    d) selecting one or more educts or products,
    e) searching through the second database for reactions in which the one or more selected educts and/or products occur, and effecting intermediate storage of said reactions,
    f) searching through the second database for reactions in which the educts and/or products of the reactions occur, which were found and put into intermediate storage in step e), and effecting intermediate storage of the reactions obtained, and
    g) preparing at least one reaction chain and/or reaction tree of the obtained reactions that contain the one or more selected educts or products.

2. A method according to claim 1, wherein the reactions are stored encoded in a manner that their code contains the encodings of the educts and products involved in the reaction.

3. A method according to claim 1, wherein allocated to the reactions and/or educts and/or products are one or more evaluation parameters, which by setting of a selection criterion for the parameter permit a selection of reactions in a chain or a branched reaction tree.

4. A method according to claim 3, wherein the one or more evaluation parameters are stored as part of the code.

5. A method according to claim 3, wherein the one or more evaluation parameters are selected as measurement numbers for one or more of the following properties:
    toxicity, a reaction condition, apparatus expenditure, yield, costs of manufacture and/or procurement, stability of the educts and/or products, and handleability of the educts and/or products.

6. A method according to claim 1, wherein an optimization program prepares one or more optimized synthesis paths.

7. A method according to claim 4, wherein an optimization program prepares one or more optimized synthesis paths.

8. A method according to claim 5, wherein an optimization program prepares one or more optimized synthesis paths.

9. A method according to claim 1, further comprising searching through the second database one or more times after step f) for reactions in which the educts or products of the reactions occur, which were found and put into intermediate storage in the step immediately preceding the current step, and effecting intermediate storage of the reactions obtained.

10. A computer program that generates one or more synthesis paths by the method of claim 1.

* * * * *